United States Patent
Withiam et al.

(10) Patent No.: US 7,718,184 B2
(45) Date of Patent: May 18, 2010

(54) HYDROPHOBICALLY COATED/TREATED METAL SILICATE ABSORBENT PARTICLES AND PERSONAL CARE COMPOSITIONS THEREOF

(75) Inventors: Michael C. Withiam, Landenberg, PA (US); Donald P. Conley, Conowingo, MD (US); Michael Simone, North East, MD (US)

(73) Assignee: J.M. Huber Corporation, Atlanta, GA (US)

( * ) Notice: Subject to any disclaimer, the term of this patent is extended or adjusted under 35 U.S.C. 154(b) by 0 days.

(21) Appl. No.: 11/823,073

(22) Filed: Jun. 26, 2007

(65) Prior Publication Data

US 2007/0254039 A1 Nov. 1, 2007

Related U.S. Application Data

(63) Continuation of application No. 11/050,237, filed on Feb. 3, 2005, now Pat. No. 7,303,766.

(51) Int. Cl.
| | |
|---|---|
| *A61K 8/02* | (2006.01) |
| *A61K 8/03* | (2006.01) |
| *A61K 8/18* | (2006.01) |
| *A61K 8/19* | (2006.01) |
| *A61K 8/25* | (2006.01) |
| *A61K 8/26* | (2006.01) |
| *A61K 8/28* | (2006.01) |
| *A61K 8/84* | (2006.01) |
| *A61K 8/92* | (2006.01) |

(52) U.S. Cl. ............ 424/401; 514/769; 514/770; 514/772.4; 514/782; 514/784

(58) Field of Classification Search .......... None
See application file for complete search history.

(56) References Cited

U.S. PATENT DOCUMENTS

| 5,160,742 | A | * | 11/1992 | Mazer et al. ............... 424/469 |
|---|---|---|---|---|
| 5,298,234 | A | * | 3/1994 | Nakazawa et al. .......... 423/714 |
| 5,618,522 | A | * | 4/1997 | Kaleta et al. ............... 424/60 |
| 5,631,013 | A | * | 5/1997 | Bergmann et al. ......... 424/401 |
| 5,891,235 | A | * | 4/1999 | Suzuki et al. .............. 106/483 |
| 7,303,766 | B2 | | 12/2007 | Withiam et al. |
| 7,303,767 | B2 | | 12/2007 | Withiam et al. |
| 2003/0049218 | A1 | * | 3/2003 | Patel et al. ................. 424/65 |

FOREIGN PATENT DOCUMENTS

FR 2854324 A1 * 11/2004

OTHER PUBLICATIONS

Siegfried, R. "Economical Sebum Absorption Technology", PCIA, Personal Care Ingredients, Asia, Mar. 9-11, 2004, abstract.*
Office Action in U.S. Appl. No. 11/050,237, dated Jun. 8, 2007.
Notice of Allowance in U.S. Appl. No. 11/050,237, dated Oct. 3, 2007.
Office Action in U.S. Appl. No. 11/050,238, dated May 4, 2006.
Office Action in U.S. Appl. No. 11/050,238, dated Jun. 8, 2007.
Notice of Allowance in U.S. Appl. No. 11/050,238, dated Oct. 3, 2007.

* cited by examiner

*Primary Examiner*—Ernst V Arnold
*Assistant Examiner*—James Henry Alstrum-Acevedo
(74) *Attorney, Agent, or Firm*—Cheryl J. Tubach; Patricia L. Ades

(57) ABSTRACT

Coated particles of metal (such as calcium) silicate that exhibit excellent odor neutralization and sebum absorption properties when present within certain cosmetic and/or personal care formulations and suspensions are provided. Uncoated calcium silicate exhibits a high pH level that may have a deleterious effect upon such cosmetic and/or personal care compositions, thereby rendering the overall composition ineffective for its intended purpose, particularly if the calcium silicate is present in its usual state at high loading levels. Alternatively, if certain materials present within personal care compositions exhibit a sufficiently low pH level, the effectiveness of such calcium silicates may be compromised as well. Such novel coated/treated calcium silicates thus permit high loadings of this beneficial odor neutralizing/sebum absorbing additive within cosmetic and/or personal care formulations without causing any appreciable instability issues or viscosity modification concerns or allow for coexistence with such low pH materials without any appreciable reduction in performance capabilities of the calcium silicates themselves. Certain personal care compositions comprising these novel coated calcium silicate particulates are encompassed within this invention as well.

12 Claims, No Drawings

HYDROPHOBICALLY COATED/TREATED METAL SILICATE ABSORBENT PARTICLES AND PERSONAL CARE COMPOSITIONS THEREOF

CROSS-REFERENCE TO RELATED APPLICATIONS

This is a continuation of U.S. application Ser. No. 11/050,237, filed Feb. 3, 2005 now U.S. Pat. No. 7,303,766, the content of which is incorporated herein by reference in its entirety for all purposes.

FIELD OF THE INVENTION

This invention pertains to coated particles of metal (such as calcium) silicate that exhibit excellent odor neutralization and sebum absorption properties when present within certain cosmetic and/or personal care formulations and suspensions. Uncoated calcium silicate exhibits a high pH level that may have a deleterious effect upon such cosmetic and/or personal care compositions, thereby rendering the overall composition ineffective for its intended purpose, particularly if the calcium silicate is present in its usual state at high loading levels. Alternatively, if certain materials present within personal care compositions exhibit a sufficiently low pH level, the effectiveness of such calcium silicates may be compromised as well. Such novel coated/treated calcium silicates thus permit high loadings of this beneficial odor neutralizing/sebum absorbing additive within cosmetic and/or personal care formulations without causing any appreciable instability issues or viscosity modification concerns or allow for coexistence with such low pH materials without any appreciable reduction in performance capabilities of the calcium silicates themselves. Certain personal care compositions comprising these novel coated calcium silicate particulates are encompassed within this invention as well.

BACKGROUND OF THE INVENTION

A broad array of topical personal care and personal hygiene products are available for application to human skin to counteract malodors associated with the human body, particularly those malodors resulting from and associated with perspiration. These products include sports and athletic sprays and powders, antiperspirants, foot and body powders, body sprays, and especially deodorants. Other types of products are available to absorb potentially destructive sebum oils and residues generated by the sebaceous glands within a person's skin. The ability to combat either of these undesirable results is quite favorable within the personal hygiene product industry and the search for new and effective additives for such purposes has existed for many years.

As examples, malodors may be "masked" or concealed by placing a sufficient amount of perfume composition in the deodorant in order to hide or cover the malodor. Perfumes provide the additional benefit of imparting a desirable fragrance, such as a variety of different fresh, pastoral, or musk scents, to a cosmetic or personal care product. However, "masking" also has distinct limitations. Unfortunately, some malodors cannot be masked simply by adding perfumes, because they are highly volatile (and therefore diffuse quickly into the air) or because they are extremely potent. Indeed, in some cases it may be impossible to add sufficient amounts of perfume in order to sufficiently conceal the underlying malodor without also giving the personal care product an overly strong, perfumed odor. Topical antimicrobials, such as triclosan, may also be applied to the skin since perspiration-associated body malodors are typically the result of interaction between microbes, perspiration and triglyceride secretions from the sebaceous glands, which combine to produce malodorous and pungent metabolites and/or fatty acids. Thus, by controlling the microbe population on the skin's surface, the malodor can be eliminated or reduced in intensity. However, the use of antimicrobial agents, particularly in excessive amounts, is strongly discouraged because it may contribute to the development and/or selection of microbes resistant to known antimicrobial compounds. Additionally, the build-up of antimicrobial agents in the human body is suspected of potentially producing heretofore unknown side effects. Furthermore, the general molecular structures of some antimicrobials have been reported to cause skin irritation, obviously a result unwanted within skin treatment and personal hygiene formulations.

Another approach that avoids the aforementioned problems while also reducing malodor involves the use of odor absorbers, such as activated charcoal and zeolites. These odor absorbing compounds function by absorbing odors and perspiration, and unlike the aforementioned treatment compounds they do not irritate the skin or impart an overly perfumed scent to the composition. However, charcoal and zeolite odor absorbers have the disadvantage that as they get wet (e.g., they come into contact with perspiration) they can become ineffective at odor absorption. For similar reasons, these odor absorbers can also be difficult to formulate into compositions that contain even small quantities of water.

It had been realized that metal silicate additives provide excellent malodor protection as well as potential sebum absorption benefits within cosmetic, etc., compositions, such as within skin care and decorative cosmetics, as some examples. Unfortunately, it was also realized that such silicate materials generally exist at high pH levels that create problems for such formulations and compositions, particularly when they are present in amounts that are necessary for the desired malodor neutralization and/or sebum absorption benefits to occur during use. As a result, such materials may cause deleterious reactions and stability problems within such cosmetic, personal hygiene, skin treatment, etc., formulations and compositions (such as, as one example, rendering ineffective certain pH sensitive antiperspirant salts). Furthermore, certain materials, in particular antiperspirant salts, may deleteriously affect the performance of such malodor reducing compounds through ionic interaction between the cation of the metal silicate and the anion of the antiperspirant salt. It has been noticed that certain amounts of antiperspirant salts will gel, coagulate, or otherwise precipitate out of solution during storage when present simultaneously with uncoated/untreated metal (i.e., calcium) silicates. Although the amount of such antiperspirant salts is generally much higher than for the malodor-reducing calcium silicates, the overall effect has been found to render such calcium silicates less effective for their intended purpose and to reduce (although relatively slightly) the amount of the available salts for eventual precipitation on the target skin surface. There is thus a clear need to provide calcium silicate additives for such types of personal care compositions that exhibit lower pH levels during application of finished product forms in order to ensure the maximum effectiveness of all the additives present within such formulations. To date, no such improvement has been provided within the cosmetic formulation and/or personal hygiene product industries.

OBJECTS OF AND BRIEF SUMMARY OF THE INVENTION

It is therefore one object of this invention to provide metal, and preferably, though not necessarily, calcium, silicate particles that, when in a dispersion form within a cosmetic and/or deodorant formulation, and present at a concentration suitable to permit malodor neutralization from a person's skin, exhibits a pH level sufficiently low as not to destabilize or alter the functionality of other ingredients present within the target finished cosmetic and/or deodorant formulations.

Accordingly, the present invention encompasses particulate metal (again, preferably, though not necessarily, calcium) silicate materials that are at least partially coated with an organic film. Such a film should exhibit either a) an ability to erode when subjected to sufficient pH changes or b) sufficient porosity to permit migration of metal ions or isovaleric acid there through. The invention also encompasses includes a fluid or solid personal care product comprising such a coated/treated metal (i.e., calcium) silicate material and a vehicle. Additionally, this invention encompasses a deodorant formulation comprising such a coated/treated metal (i.e., calcium) silicate material and at least one antiperspirant salt. The invention also includes a method of inhibiting body odor by applying to the skin an effective amount of a personal care composition comprising such coated/treated metal silicate materials.

DETAILED DESCRIPTION OF THE INVENTION

All parts, percentages and ratios used herein are expressed by weight unless otherwise specified. All documents cited herein are incorporated by reference.

By "personal care compositions" it is meant compositions that comprise at least one material (in addition to the inventive coated/treated calcium silicates) that is typically utilized for the treatment of a person's skin (such as, as examples, skin softeners, antiperspirant salts, cosmetics, and the like). Types of such personal care compositions include, without limitation, either fluid or solid in nature, deodorants, anti-perspirants, athletic sprays, body sprays, hair conditioners, shampoo, skin conditioners, body washes, liquid bath soaps, facial cleansers, make-up removers, baby baths, hand soaps, make-up foundation, skin-coloring formulations, sunscreens, and the like.

It has been determined that coating metal silicate materials (a term that is intended to encompass a variety of different materials, including, without limitation, calcium silicate, calcium aluminosilicate, calcium zinc silicate, magnesium silicate, magnesium zinc silicate, and calcium magnesium silicate; this term is further elaborated upon below) permits the inclusion of relatively high amounts of such materials within personal care compositions in order to provide effective benefits associated with such materials as well as not impair the effectiveness of the other components present within the same formulations nor deleteriously affect the effectiveness of the metal silicates when present with low pH (~4.5 pH, for example) ionic materials. For purposes of this invention, the term "calcium silicate" shall indicate any metal silicate that includes at least calcium, magnesium, or zinc cation therein; thus, any compounds that include further metal cation species, such as aluminum, zinc, magnesium, etc., are considered to be within this definition.

Additionally, particulate metal silicate materials frequently exhibit other problems during composition manufacture as well as during storage and use. For example, uncoated materials of such type have been known to prove difficult to properly disperse without created precipitates within the bottom of the fluid container and, as noted above, the high pH levels of such uncoated materials can effectively destabilize the overall composition or at least impair the effectiveness of some if not all of the individual active ingredients present therein.

Surprisingly, then, it was also determined that coating, even partially, such calcium silicate materials prior to inclusion within a personal care composition actually aids in the incorporation of such materials therein, more rapidly disperses to provide greater homogeneity within the target formulation, and does not exhibit any appreciable propensity to destabilize such lower pH compositions. Furthermore, even more surprisingly, the presence of a coating on such calcium silicate materials did not appreciably reduce the ability of such additives to absorb malodors (particularly isovaleric acid) as compared with uncoated calcium silicate particulates. Even more importantly, it was discovered that the minimum level of coating needed for proper functioning in these respects did not show any effects on the viscosity of the target personal care formulations (if fluid in nature) either (as opposed to other coated materials that require certain types of film-forming coatings and in sufficiently high amounts that, upon dissolution within an aqueous- or nonaqueous-based composition the film-forming materials can actually modify the viscosity to a level undesired). Lastly, the surface characteristics of such particulate calcium silicate materials may also be modified through the utilization of such a beneficial coating such that the feel of the overall personal care composition may be altered in a favorable fashion as well.

The present invention includes topical personal care compositions comprising a coated metal silicate along with at least one acceptable vehicle (such as diluents or carriers) for the odor-absorbing calcium silicate, so as to facilitate the calcium silicate's distribution when the composition is applied to the skin. (Suitable vehicles, as well as other suitable personal care composition ingredients are discussed in greater detail, below). The silicates act as odor absorbents and neutralizers to absorb and neutralize body malodors, particularly body malodors associated with perspiration. By incorporating these calcium silicates, a wide variety of personal care compositions may be produced that provide effective, long-lasting absorption and neutralization of odors. This allows effective body malodor suppression without the overuse of perfumes or antimicrobial agents. In addition to these benefits, the calcium silicate also improves the "feel" of personal care compositions in which it is incorporated. Particularly, the personal care compositions have a smoother feel when applied and in contact with the skin.

That personal care compositions incorporating the inventive coated/treated metal silicates are capable of providing effective odor neutralization and suppression would itself be surprising to a person of ordinary skill in the art. This is because the particulate calcium silicates are coated with several other ingredients, and thus would seem incapable of neutralizing and suppressing body malodors. However, by the present invention, personal care compositions have been formulated that fully incorporate coated/treated calcium silicate particles without diminishing the ability of the calcium particles to absorb and neutralize odors.

As noted above, the coated/treated metal (i.e., calcium) silicates in the cosmetic compositions prepared according to the present invention absorb both malodors originating from human skin as well as absorb the fatty acids found on the skin even while such compounds comprise barriers to direct contact with the molecular surfaces to which malodors and fatty acids readily react. Calcium silicates, as a preferred example of a preferred metal silicate, are believed to offer two measures to neutralize body malodors: they not only absorb the malodors themselves, but they also reduce the quantities of fatty acids that are part of the cause of the malodors. It is believed that such malodorous compounds are attracted into the intraparticle pores and interstices that are formed within the calcium silicates. The molar composition of the metal silicate materials permits dissociation of the metal cation and the silicate anion. Such freed metal cations (such as calcium, magnesium zinc, etc.) can then react with the available anions (such as long-chain fatty acids, for instance isovaleric acid) of the targeted malodor-creating compounds to create low-volatility salts. As a result, such newly formed salts exhibit reduced volatility into the surrounding environment, and, ultimately, the chances of smelling such non-volatized compounds are drastically reduced if not prevented.

The organic films (coatings) applied to the calcium silicates thus surprisingly provide protection for the other pH sensitive ingredients present within such personal care compositions while also exhibiting the ability to permit such calcium silicates to absorb malodors and/or sebum from treated skin. While not wishing to be limited by theory, it is believed that the present organic films do in fact provide protection from low pH materials by providing at least a partial barrier to any such contact with low pH components, whereas such films also exhibit the tendency to either erode over time while in solution (upon contact with water or upon exposure to materials exhibiting significantly different pH levels) or after application to a person's skin (upon exposure to changes to pH levels, such as contact with acids present on skin, such as isovaleric acid, or as contact with high pH perspiration) or to exhibit sufficient porosity to permit diffusion of calcium ions through such a barrier film from the calcium silicate, or to permit the targeted acids to diffuse through the barrier film to the calcium silicate. Similar results exist for the other metal silicates included within this class of compounds intended for utilization within this invention.

These metal silicates are most typically prepared by the reaction of a reactive silica with an alkaline earth metal reactant, preferably an alkaline earth metal oxide or hydroxide, and a source of aluminum such as sodium aluminate or alumina. Such materials can generally be represented by the formula $Ca_xM_ySiO_z$, wherein M is one of more multivalent cations selected from Mg, Al, and Zn, preferably Mg, and x is the number of moles of the calcium cations and is between 0 and 4, preferably between 0.5 and 2, y is the number of moles of such other metal cations and is between 0 and 4, z is the number of moles required to balance the overall charge of the metal cations, and x+y is from 0.5 to 6, preferably from 1 to 4, most preferably from 1 to 2. Because the final properties of the silicate are dependent on the reactivity of the silica, the silica source is preferred to be the reaction product of a soluble silicate, such as, but not limited to sodium silicate, and a mineral acid, such as sulfuric acid. Suitable synthetic amorphous alkaline earth metal silicates are manufactured by the J. M. Huber Corporation and are sold in different grades under the trademark HUBERDERM®. Methods and techniques for preparing these silicates are discussed in greater detail in U.S. Pat. No. 4,557,916. Other suitable amorphous silicates are available from J. M. Huber Corporation such as sodium aluminosilicate sold under the trademark ZEOLEX® and sodium magnesium aluminosilicate sold under the trademark HYDREX®. HUBERDERM® 1000, a calcium silicate, is also available from J.M. Huber Corporation. The odor absorption and neutralization properties of some of these materials are discussed in greater detail in the Examples, below.

Personal care compositions prepared according to the present invention comprise about 0.5 wt % to about 20 wt %, preferably about 1 wt % to about 10 wt % of the odor neutralizing metal silicate. In addition to the metal silicate, the present personal care compositions will also comprise one or more dermatologically acceptable cosmetic ingredients.

The coating materials to be applied may be selected from the group of suitable organic hydrophilic polymers for coating, include starch, gum arabic, gum karaya, gum tragacanth, guar gum, locust bean gum, xanthan gum, carrageenan, alginate salt, casein, dextran, pectin, agar, sorbitol, 2-hyroxyethyl starch, 2-aminoethyl starch, maltodextrin, amylodextrin, 2-hydroxyethyl cellulose, methyl cellulose, carboxymethyl cellulose salt, cellulose sulfate salt, chitosan, chitosan acetate, polyvinylpyrrolidone, polyethylene glycol, polypropylene glycol, polyethylene oxide, polyvinyl alcohol/acetate, polyacrylamide, and the like. Such hydrophilic polymers exhibit the proper degree of erodibility when in solution or when applied to a persons' skin and subsequently (or simultaneously) subjected to pH changes due to perspiration. Others in this list exhibit sufficient porosity when applied to the metal silicate materials to permit migration of metal ions therethrough or, preferably, the migration of isovaleric acid therethrough in order for the silicate to neutralize such an undesirable odor-producing compound. Polyvinyl acetate is illustrative of a water-insoluble polymer which can be included as an additional coating component to moderate the hydrophilicity of a hydrophilic polymer coating. One skilled in the art will appreciate other various hydrophilic polymers that are within the scope of the present invention.

Suitable water-insoluble (hydrophobic) organic materials, alone or in combination with one or more other components, for producing films for at least partially coating such absorbent particles include polyvinyl acetate, polyacrylamide, polyvinyl chloride, polystyrene, polyethylene, polymethacrylate, paraffin wax, carnauba wax, beeswax, stearyl alcohol, zein, shellac, edible fat, $C_8$-$C_{24}$ fatty acids (for example butyric acid, palmitic acid, lauric acid, stearic acid, isostearic acid) and their alkali metal salts (i.e. sodium stearate), and the like. As for the hydrophilic polymers listed above, these films exhibit the proper degree of erosion upon exposure to sufficient shifts in pH, as well as certain degrees of porosity for proper functioning of the metal silicate materials even when coated.

Either type of film may be utilized, as well as combinations thereof in order to provide the proper degree of erodibility while in solution or when applied to a target skin surface, or to exhibit the proper degree of porosity for the diffusion of the desired acids or the diffusion of the calcium ions. As such, any degree of coating may be utilized. Complete coating would be preferable when the metal silicate materials are subject to significantly low pH levels in solution and the film materials permit effective porosity, as noted above, or erode at a proper rate in order to permit as efficient use of the benefits available from such calcium silicate materials by the user. Partial coating can thus be performed as well, particularly if the solution in which the metal silicate materials are present do not present as drastic a pH shift, as well as wherein the organic films themselves exhibit lower degrees of porosity. Any level of selection of porosity, coating, etc., may thus be followed and would be well within the purview of the ordinarily skilled artisan for such a purpose.

Such materials may be applied in any manner, such as, as non-limiting examples, coating or encapsulation techniques, including fluid-bed coating, spray drying or film coating, spray drying and spray chilling, microencapsulation, coacervation and phase-separation processes, fluid bed coating (such as, without limitation, Wurster air-suspension coating), interfacial polymerization processes, co-extrusion microencapsulation processes, and spinning disc coating. Preferably, spray drying or fluid-bed coating.

The degree of coating may be controlled through application of the desired weight percentage of polymer or other additives using techniques well understood by those in the coating field. The minimum level required for proper functioning will vary depending on the type of coating and the desired protective effect. Preferably, the coating level will be between 1% and 30%, more preferably between 0.5% and 15%. A continuous (completely coated)-erodible or selectively porous organic film (such as carboxymethylcellulose, as one non-limiting example) is preferable for compositions of antiperspirant salts and these inventive materials, again as one non-limiting example. The level of coating is not altogether critical as much as the materials should be designed to achieve the goals of the ultimate formulator for the target personal care composition. Thus, although these levels are suggestions, the coating level itself should be sufficient ultimately to provide protection from low pH ingredients, as well as protect pH sensitive components therein, to provide a certain degree of timed release of the calcium silicate materials themselves when in solution and when applied to a user's skin, and/or to aid in flow, suspension, or sensory properties for the overall composition.

Dermatologically acceptable cosmetic ingredients include first and most importantly a diluent or carrier. The vehicle, diluent or carrier may be selected from a wide range of ingredients. The vehicle may comprise water and/or a water-miscible or dispersible organic liquid or liquids and alternatively or additionally a water-immiscible liquid or liquids and waxes. The cosmetically acceptable vehicle will preferably form from 80% to 99% by weight of the composition, and can, in the absence of other cosmetic adjuncts, form the balance of the composition. The vehicle may be aqueous, non-aqueous or a combination of both, such as an emulsion. In a combination vehicle, an oil or oily material may be present, together with one or more emulsifiers to provide either a water-in-oil emulsion or an oil-in-water emulsion, depending largely on the average hydrophilic-lipophilic balance (HLB) of the emulsifiers employed. This also includes multiple emulsions: water-in-oil-in-water or oil-in-water-in-oil emulsions. For sebum absorption purposes, it is important that the inventive coated/treated calcium silicate not be present within the oil phase of any emulsion since such calcium silicates would be exhausted in terms of absorbing the oil portion of such a formulation prior to any chance of properly performing after application to a person's skin.

In the case where the composition contains a combination of aqueous and non-aqueous vehicle components, the aqueous phase can be from about 90 wt. % to about 10 wt. % of the vehicle, as can the non-aqueous phase. In an embodiment of the invention where the vehicle is aqueous or is comprised of a mixture of aqueous and non-aqueous components, preferably the vehicle is at least 80 wt % water, by weight of the vehicle. Preferably, water comprises at least 85 wt % of the inventive composition, and most preferably from 90 to 95 wt % of the composition.

In an embodiment of the invention where the vehicle is comprised of non-aqueous components, the dermatologically acceptable non-aqueous cosmetic ingredients in the vehicle will usually form from 80% to 99.9% by weight of the composition, and may, in the absence of other cosmetic adjuncts, form the balance of the composition.

Examples of suitable non-aqueous carriers may include alcohols, polyalkoxylated glycols (such as propylene glycol), volatile and nonvolatile liquid silicone carriers (such as cyclicsilicone polymers), hydrocarbon and mineral oils and branched chain hydrocarbons. Specific, non-limiting examples of organic liquids suitable for use include octyldodecanol, butyl stearate, diisopropyl maleate, and combinations thereof. Also suitable for use are acrylic acid-based polymers.

It is desirable that the odor absorbing ingredient in the inventive compositions remains substantially localized in the region of the body to which it has been topically applied. In order to assist this to happen and also to enable alternative dispensers for the composition to be employed, the vehicle may be thickened or structured, for example by introducing one or more materials for that purpose. Thickened or structured compositions commonly adopt the form of firm sticks, soft solids and creams. In such circumstances, the materials are often referred to as structurants or gellants and may sometimes alternatively be called thickeners, depending on the final form of the composition. The vehicle may be further diluted with a volatile propellant and used as an aerosol; may be mixed with an additional liquid and/or other ingredients and used, for example, as a roll-on or squeeze-spray product; or mixed with one or more thickeners and/or structurants and used, for example, as a gel, soft solid, or solid stick product.

Exemplary thickeners are cross-linked polyacrylate materials available under the trademark CARBOPOL® from the B. F. Goodrich Company. Gums may be employed such as xanthan, carrageenan, gelatin, karaya, pectin and locust beans gum. Under certain circumstances, the thickening function may be accomplished by a material also serving as a carrier or emollient vehicle. For instance, silicone gums in excess of 10 centistokes and esters such as glycerol stearate have such dual functionality. A thickener will usually be present in amounts anywhere from 0.1 to 20% by weight, preferably from about 0.5% to 10% by weight of the composition.

Other dermatologically acceptable cosmetic ingredients include rheology affecting agents such as solidifying agents and gellants. The solidifying agents act to provide solidity to a personal care composition so that they are in solid (or semi-solid) form at room temperature. Suitable solidifying agents include especially high melting point waxes (melting points between 65° C.-110° C.) which include hydrogenated castor oil, paraffin, synthetic wax, ceresin, beeswax, and other such waxes. Also acceptable are low melting point waxes (melting points between 37° C.-65° C.), which include fatty alcohols, fatty acids, fatty acids esters, fatty acid amides, and the like.

Gellants are used in the case of solid stick compositions, to give the stick an appropriate consistency and provide an appropriate gel matrix and product hardness at the completion of processing. The gelling agents will vary depending on the particular form of the personal care composition and whether the personal care composition is aqueous or non-aqueous. Suitable gellants include esters and amides of fatty acid or hydroxy fatty acid gellants, fatty acid gellants, salts of fatty acids, esters and amides of fatty acid or hydroxy fatty acid gellants, cholesterolic materials, lanolinolic materials, fatty alcohols, triglycerides, substituted sorbitol acetal compounds, such as mono- and/or di-benzylidene sorbitols, such as, as one non-limiting example, 3,4-dimethylbenzylidene sorbitol, and other suitable solid, non-polymeric gellants. Preferred gellants (for both aqueous and nonaqueous compositions) include fatty alcohols, most preferably stearyl alcohol. Amounts of these gellant components may range anywhere from 0.001% up to 20% by weight of the composition.

The inventive compositions may contain any of a number of desired "active" ingredients, including drug substances such as anti-inflammatory agents, topical anesthetics, antimycotics, etc.; skin protectants or conditioners; humectants; and the like, depending on the intended uses for the formulations.

Antiperspirant salts possible as materials within the inventive personal care compositions include, without limitation, any aluminum astringent antiperspirant salt or aluminum and/or zirconium astringent complex can be employed herein. Salts useful as astringent antiperspirant salts or as components of astringent complexes include aluminum halides, aluminum hydroxy-halides, zirconyl oxyhalides, zirconyl hydroxy-halides, and mixtures of these materials.

Aluminum salts of this type include aluminum chloride and the aluminum hydroxyhalides having the general formula $Al_2(OH)_xQ_y \cdot XH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. No. 3,887,692 issued to Gilman on Jun. 3, 1975, and U.S. Pat. No. 3,904,741 issued to Jones and Rubino on Sep. 9, 1975.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to about 2 and need not be an integer, n is the valence of B, 2-nz is greater than or equal to 0, and B may be selected from the group consisting of halides, nitrate, sulfamate, sulfate, and mixtures thereof. Although only zirconium compounds are exemplified in this specification, it will be understood that other Group IVB metal compounds, including hafnium, can be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than zero groups per molecule.

As alluded to above, one of the more significant problems faced by utilizing calcium silicate within certain personal care compositions is the tendency of such compounds to interact with the cations and anions of low pH salts. In particular, it has been realized that antiperspirant salts exhibit both of these properties to the extent that compatibility and stability of both materials may be compromised during storage of a deodorant composition comprising both types of materials and exhibiting a resultant and sufficiently low pH (believed to be as high as 4.5 pH) to generate such deleterious ionic interactions. Since the inclusion of a malodor reducing compound within such a type of composition is beneficial, there is thus an evident need to facilitate coexistence of such materials without any appreciable loss of performance of either.

Without a coating, calcium silicates appear to react readily with the cationic species of such low pH antiperspirant salts (generally either aluminum or zirconium ions), thus eliminating the benefits accorded the user through destruction of the needed molecular structure of the calcium silicate itself. Likewise, however, the reaction of the calcium cation with the anion of the antiperspirant salt may cause precipitation of the salt out of solution prior to contact with a user's skin. Such salts generally function by remaining in solution until reacting with a sufficiently alkaline source (preferably, the perspiration on a person's skin), at which time the result is a precipitate that migrates to sweat ducts on the skin surface and "plugs" such cavities to prevent or slow the rate of perspiration. The high alkalinity of calcium silicates is sufficient to cause at least some premature precipitation, thereby rendering at least some of the salts ineffective. Such a two-way reduction in effectiveness is thus to be avoided in order to permit utilization of the full benefit of the malodor reducer and the perspiration reducer simultaneously. The inventive coated/treated calcium silicates have been found to provide such desired results as well as other benefits.

The fluid or solid personal care products prepared according to the present invention may also include other optional components. The CTFA Cosmetic Ingredient Handbook, Tenth Edition, 2004, which is incorporated by reference herein in its entirety, describes a wide variety of cosmetic and pharmaceutical ingredients commonly used in skin care compositions, and which are suitable for use in the compositions of the present invention. These optional components include pH buffering agents, additional malodor control agents, fragrance materials, dyes, and pigments, preservatives, skin aids (e.g., aloe), cosmetic astringents, liquid or solid emollients, emulsifiers, film formers, propellants, skin-conditioning agents, such as humectants, skin protectants, solvents, solubilizing agents, suspending agents, surfactants, waterproofing agents, viscosity increasing agents (aqueous and non-aqueous), waxes, wetting agents, and other optional components. Amounts of these adjunct components may range anywhere form 0.001% up to 20% by weight of the composition.

The products themselves may be formulated to be in a variety of forms, such as solid and semi-solid stick deodorants (such as emulsion sticks or suspensoid sticks), roll-on deodorants, and deodorant aerosol and pump-sprays, and even soap bars.

The personal care compositions of the present invention may be prepared by any known or otherwise effective technique suitable for providing a fluid personal care composition having the essential materials described herein. Techniques for forming such compositions are very well known in the art. The present invention is not dependent upon any particular formulation technique, it being recognized that the choice of specific formulation components may well make necessary some specific formulation procedure.

Methods for preparing the personal care compositions of the present invention include conventional formulation and mixing techniques. Many variations of formulating the compositions of the present invention exist, and all are considered within the scope of the present invention. Suitable methods include combining the calcium silicate odor absorbing/neutralizing agent with part or all of the liquid vehicle. A liquid may be entirely absorbed into the calcium silicate, and if so, additional liquid or liquids and other materials are added until the calcium silicate is evenly dispersed. A thickener or gellant is added and the composition is mixed and may be heated, if required for homogenous incorporation. Adjunct and/or additional materials may be added at this point, and the batch may be allowed to cool, if necessary. The thickened or gelled composition is allowed to viscosity or solidify in a suitable container or dispenser.

PREFERRED EMBODIMENTS OF THE INVENTIONS

Test Protocols

Where mentioned in this application, the surface area was determined by the BET nitrogen absorption method of Brunaur et al., as reported in the J. Am. Chem. Soc. 60, 309 (1938).

Organic coating treatment level is calculated from the amounts of ingredients used in the example preparation and is expressed as a weight to weight percentage.

Median particle size (MPS) was determined using a Model LA-910 laser light scattering instrument available from Horiba Instruments, Boothwyn, Pa. A laser beam is projected through a transparent cell, which contains a stream of moving particles suspended in a liquid. Light rays, which strike the particles, are scattered through angles which are inversely proportional to their sizes. The photodetector array measures the quantity of light at several predetermined angles. Electrical signals proportional to the measured light flux values are then processed by a microcomputer system to form a multichannel histogram of the particle size distribution.

Oil absorption, using linseed oil, was determined by the rubout method. This method is based on a principle of mixing oil with a silicate by rubbing with a spatula on a smooth surface until a stiff putty-like paste is formed. By measuring the quantity of oil required to have a paste mixture, which will curl when spread out, one can calculate the oil absorption value of the silicate—the value which represents the volume of oil required per unit weight of silicate to saturate the silicate sorptive capacity. Calculation of the oil absorption value was done as follows:

$$\text{Oil absorption} = \frac{\text{ml oil absorbed}}{\text{weight of silicate, grams}} \times 100$$

$$= \text{ml oil}/100 \text{ gram silicate}$$

Isovaleric acid is associated with and contributes to foot and body perspirative malodors. Commercial samples of this malodorous material was used as a model compound to assess the ability of cosmetic compositions prepared according to the present invention, comprising synthetic metal silicate materials to remove the odors associated with these malodorous materials.

Samples for in vitro odor capacity analysis were prepared as follows. Test specimens were prepared by weighing 0.25 grams of an odor absorbing/neutralizing test compound into a 20-ml crimp cap headspace sampling vial (VWR part no. 66064-348). Then 5 ml of 5% NaCl solution and an appropriate volume of isovaleric acid (Sigma-Aldrich part no. 3314699) were added to the vial. The volume of isovaleric acid was chosen such that the residual acid not neutralized will be within the linear working range, i.e. 20-100 µl (establishment of the linear working range is described below). This volume is determined from historical data, physical properties of the test substance and trial and error. The resulting mixture was then capped, vigorously agitated on a vortex agitator, shaken by hand, allowed to equilibrate for 24 hours and then analyzed using GCMS ("Gas Chromatography Mass Spectrometry").

A Hewlett Packard 5890 Gas Chromatograph with a HP5972 Mass Selector Detector was utilized for this analysis (GCMS analysis).

The sampling method used to determine the detectable quantity of non-absorbed odor causing substance (isovaleric acid) or odor neutralization capacity of each specimen was Solid Phase Microextraction (SPME) headspace analysis.

Each sample vial was sampled using a 100 µm PDMS Solid Phase Microextraction fiber, available from Supelco/Sigma-Aldrich, part no. 57300-U and a manual fiber holder, part no. 57330-U. The fiber was exposed to the vial headspace for 5 minutes at room temperature then desorbed into the GCMS (as noted above). The GC was outfitted with a Restek Stabilwax column (60 m length, 0.25 mm id., 0.25 µm df) available from Restek Corporation, Bellfonte, Pa. as part no. 10626. The GCMS system was set to the following operating conditions.

| Low Temperature Odor Capacity GCMS Operating Conditions | |
|---|---|
| For the GCMS: | |
| Temp. profile: | 4 min @ 50° C. |
| | Ramp 10° C./min to 200° C. |
| | Ramp 20° C./min to 240° C. |
| Carrier gas: | He, 24 psi |
| Injector: | 250° C. |
| | Split - 100 ml/min. |
| | 1 mm straight liner |
| Detector: | 280° C. |
| | MS scan mode 35-550 AMU |

A linear working range was established as follows. To prepare standards, vials were prepared containing 5 ml of 5% NaCl and 20, 40, 60, 80, and 100 µL of isovaleric acid. The vials of standards were then analyzed as described above and the peak area plotted against the isovaleric acid addition. Typically, a linear correlation of $R^2$=0.98 to 0.99 can be achieved.

To compensate for day to day drift in detector response, calibration was accomplished by running replicate standards at a 60 µl loading in 5 mls 5% NaCl at the beginning and end of each analytical set. The average peak area of these runs is used to calculate a single point response factor at 60 µls.

To calculate the odor neutralizing capacity of each specimen, a known amount of isovaleric acid was added to the 0.25 g specimen in 5 mls 5% NaCl. The amount added was such that the excess of isovaleric acid in the vial available for SPME analysis—i.e. not neutralized, falls close to the midpoint of the linear working range. The residual amount of acid in the vial, calculated from the 60 µl response factor was subtracted from the amount added, and divided by the specimen weight. This is the amount of isovaleric acid neutralized or the odor absorbing capacity in µl/g.

$$\mu l \text{ Residual Isovaleric Acid} = \frac{\text{Peak Area Specimen} \times 60 \ \mu l}{\text{Average Peak Area 60 } \mu l \text{ Replicates}}$$

$$\mu l/g \text{ Isovaleric Acid Neutralized} = \frac{\text{Isovaleric Acid Added} - \text{Residual Isovaleric Acid}}{\text{Specimen Weight, g}}$$

Coated Particulate Production

EXAMPLES 1-2

In these examples, calcium silicates were produced in-situ with an organic polymer coating. In a first step of these examples, amorphous silica suitable for use in the production of the inventive calcium silicates was prepared by adding sulfuric acid to a dilute waterglass solution in a well-agitated mixing vessel to affect the precipitation of amorphous hydrated silica. Specifically, a total of 1052 liters of sulfuric acid at a concentration of 11.4% was added at a rate of 17.8 lpm to 1893 liters of waterglass solution (3.3 $SiO_2/Na_2O$ mole ratio) containing 13% sodium silicate solids while mixing at a temperature of 83° C. The addition of the sulfuric acid was continued until a pH of 5.5 was obtained, and the reaction mixture was digested for 1 hr. The resulting suspension of silica particles was recovered by filtration, and washed and dried to form a finely divided reactive silica powder. It is equally useful to retain the undried material in the form of a filtered cake, as an intermediate material for subsequent synthesis.

The reactive silica produced above was then slurried in water to 14.56% solids content and 616 g of this silica slurry was added to a reaction vessel equipped with a constant torque agitator and paddle blades and a specified amount of a polymer and water were added to the reactor. The mixture was brought to 70° C. and digested for 5 minutes. Then 292 g of lime slurry at 16.2% solids were added to the reactor. The reactor temperature was raised to 95° C. and the reaction mixture digested for 1 hour. The resulting coated calcium silicate ($CaSiO_3$) was then filtered and dried overnight at 150° C., then milled in a coffee mill.

The amount of water and specific polymer for Example 1 and 2 are given in Table 1 below.

TABLE 1

| | Example 1 | Example 2 |
|---|---|---|
| Water, g | 1270.7 | 1270.7 |
| 1% CEKOL ® 2000 CMC, g | 136.9 | 0 |
| 1.17% CHITOLINK ® 501, g | 0 | 117 |

Several properties of Example 1 and 2 products, as well as the properties of a control sample that was made by the same procedure without any polymer addition were determined according to the methods described above and are summarized in Table 2 below.

TABLE 2

| | Example No. | | |
|---|---|---|---|
| | 1 | 2 | Control |
| Organic Treatment | CEKOL ® 2000 | CHITOLINK ® 501 | None |
| % Treatment | 1 | 1 | 0 |
| Odor Neutralization (µl/g) | 917 | 817 | 918 |
| 5% pH | 9.45 | 9.43 | 10 |
| BET, $M^2/g$ | 115 | 95 | — |
| MPS, µm | 10.2 | 11.3 | — |

CEKOL® 2000 is sodium carboxymethyl cellulose available from Noviant B.V., Nijmegen, the Netherlands and CHITOLINK® 501 is 1% chitosan acetate available from Marine Extract, Ltd, Shippagan, New Brunswick, Calif.

It is seen in Table 2 above that the odor neutralization capacity of Example 1 and Example 2 is comparable to the control sample (no treatment), however the pH was reduced significantly.

EXAMPLES 3-5

In these examples, already formed calcium silicate was post-treated with different treatment amounts of various sodium carboxymethyl cellulose polymers to reduce the product pH. HUBERDERM® 1000 calcium silicate ($CaSiO_3$) available from J.M. Huber Corporation, Havre de Grace, Md., was added to water to form a slurry in an agitated vessel using a constant torque agitator fitted with paddle blades. To this slurry, a CMC solution was added with additional water. The resultant mixture was heated to 95° C. and digested for 60 minutes. Finally, the resultant product was recovered by filtration, washed with 2 liters hot water, and then dried overnight at 50° C. The process variables for Examples 3 to 5 are summarized in Table 3.

TABLE 3

| Process Parameters | | | |
|---|---|---|---|
| | Example | | |
| | 3 | 4 | 5 |
| Organic Treatment | CEKOL ® 500T | CEKOL ® 700 | CEKOL ® 2000 |
| % Treatment | 5 | 5 | 5 |
| Calcium Silicate, g | 100 | 100 | 100 |
| Water, g | 900 | 900 | 900 |
| CMC solution, g | 167 | 250 | 500 |
| CMC concentration, % | 3 | 2 | 1 |
| Water added, g | 150 | 0 | 0 |

CEKOL® 500T, 700 and 2000 carboxymethylcellulose (CMC) products are available from Noviant B.V., Nijmegen, the Netherlands. Examples 3-5 and an untreated HUBERDERM® 1000 calcium silicate control were tested according to the methods described above. The analysis results are summarized in Table 4 below. As above, the pH of the treated materials was reduced significantly when compared to the control.

TABLE 4

| | Example 3 | Example 4 | Example 5 | Control |
|---|---|---|---|---|
| Treatment | 5% CEKOL ® 500T | 5% CEKOL ® 700 | 5% CEKOL ® 2000 | none |
| Odor Neutralization, (µl/g) | 961 | 992 | 975 | 918 |
| 5% pH | 9.1 | 9.1 | 9.35 | 10 |
| BET, $M^2/g$ | 76 | — | 133 | — |
| MPS. µm | 4.8 | — | 9.1 | — |

EXAMPLE 6

In this example, calcium silicate was post-treated with cross-linked chitosan to reduce the product pH. Into a vessel equipped with a high shear mixer (Silverson model L4R available from Silverson Machines, Ltd., Waterside, Chesham, Bucks, UK) was added 23.7 g HUBERDERM® 1000 calcium silicate ($CaSiO_3$), 60 g water and 100 g of a mixture of 5% NaOH in methanol. The Silverson mixer was turn on and the mixture was stirred at 6000 rpm. While mixing, 90 g of a solution prepared by dissolving 2.5 g chitosan (available from ICN Biomedical, Inc., Aurora, Ohio) and 2.5 g glycine in 100 g of aqueous 2% acetic acid was added to this slurry. The mixture was digested for 10 minutes with stirring continued. The resultant product was filtered, reslurried in hot water, then re-filtered and washed with cold water and dried overnight at 50° C. The dried product was milled then reslurried in 200 g hot water and 100 ml of 25% glutaraldehyde and digested for 10 minutes at 50° C. The product was recovered by filtration, washed with hot water, slurried in water and re-filtered and washed with cold water and dried at 50° C. overnight.

The resultant product containing 5% cross-linked chitosan was analyzed according to the methods described above and had a pH of 9.2 and an odor neutralization capacity of 970 μl/g.

EXAMPLE 7-8

In these examples, already formed calcium silicate was post-treated with different treatment amounts of various soluble polymers and tested for ease of dispersion into aqueous and non-aqueous cosmetic systems. The calcium silicate was a 2.0 mole ratio $Ca_2$:$SiO_4$ product produced by adding a total of 1052 liters of sulfuric acid at a concentration of 11.5% at a rate of 17.8 lpm (liters per minute) to 1893 liters of waterglass solution (3.3 $SiO_2$/$Na_2O$ mole ratio) containing 13% sodium silicate solids while mixing at a temperature of 95° C. The addition of the sulfuric acid was continued until a pH of 5.5 was obtained, and the reaction mixture was digested for 1 hr. The resulting suspension of silica particles was recovered by filtration, and washed and dried to form a finely divided reactive silica powder.

95.3 kg reactive silica produced above was then slurried in water to 17.7% solids in a reaction vessel equipped with a constant torque agitator and paddle blades. Then 512 kg water and 233.8 kg lime slurry at 18.7% solids were added to the reactor. The reactor temperature was raised to 95° C. and the reaction mixture digested for 60 minutes. The resulting calcium silicate was then filtered, dried and milled.

A portion of the 2.0 mole ratio $Ca_2$:$SiO_4$ prepared above was retained as a control. Another portion was treated with CMC by adding 100 g calcium silicate to 900 g water in an agitated vessel using a constant torque agitator and paddle blades. To this slurry was added 167.3 g of 3% CEKOL® 500T CMC and 200 g water. The mixture was heated to 95° C. and digested for 60 minutes, before being recovered, by filtration, then washed, and dried. This 2 mole ratio calcium silicate treated with 5% CMC was EXAMPLE 7.

Another portion of the 2 mole ratio calcium silicate prepared above was treated with isostearic acid by mixing 100 g of calcium silicate with 10 g liquid isostearic acid until homogenous. This 2 mole ratio calcium silicate treated with 10% isostearic acid was EXAMPLE 8.

The untreated control calcium silicate was compared to inventive Example 7 and 8 in different cosmetic systems by gently mixing (with a Teflon stir bar) 1 g calcium silicate into 50 g of a cosmetic system, wherein the aqueous system tested was Dow Corning 1202, volatile silicone fluid and the non-aqueous system tested was light mineral oil. The time was recorded for the pigment to be completely and uniformly dispersed with results summarized in Table 5.

TABLE 5

| Sample | Treatment | System | Time to Dispersion, min |
|---|---|---|---|
| Control | None | Silicone Fluid | >10 |
| Example 7 | 5% CMC | Silicone Fluid | 7.2 |
| Control | None | Mineral Oil | 5 |
| Example 8 | 10% Isostearic acid | Mineral Oil | 3.5 |

The above data shows that the inventive treated calcium silicates of Examples 7 and 8 were dispersed into both aqueous and non-aqueous systems more quickly than the control untreated calcium silicate. In fact, the untreated calcium silicate did not disperse uniformly into the silicone fluid in even 10 minutes.

EXAMPLE 9

In this example, the odor neutralization capacity of sodium stearate and sodium stearate containing calcium silicate were compared. The Example 9 sodium stearate/calcium silicate product was prepared by mixing 90 g of sodium stearate with 10 g of calcium silicate ($Ca_2SiO_4$ prepared as a precursor in Example 7-8).

Samples of Example 9 and the sodium stearate control were analyzed using the low temperature GCMS protocol described above. Isovaleric acid (50 μl & 100 μl) was added separately to two dry powder specimens of each of the control and Example 9. The vials were capped, agitated using a vortex mixer to distribute the acid, and then allowed to equilibrate for 2 hrs at room temperature prior to sampling. The vials were then sampled for 5 minutes at room temperature using a 100 μm PDMS SPME fiber and desorbed into the GCMS under the conditions described above. Since this example is a head to head comparison, only the raw GCMS peak areas for isovaleric acid were compared. The results are summarized below in Table 6.

TABLE 6

| Sample ID | Isovaleric Acid added, μls | GC Peak Area |
|---|---|---|
| Sodium Stearate control | 50 | 18,333,024 |
| Example 9 | 50 | 308,153 |
| Sodium Stearate control | 100 | 19,162,081 |
| Example 9 | 100 | 2,595,075 |

It is seen from the data in Table 6 that Example 9 showed very significant reduction of isovaleric acid detection as compared to the sodium stearate control samples.

EXAMPLE 10-11

In these examples, calcium silicate ($Ca_2SiO_4$ prepared as a precursor in Example 7-8) materials were coated with CMC, starch, or left uncoated.

For Example 10, the calcium silicate was coated in a Glatt fluid bed coater (model GPCG-1 available from Air Techniques, Ramsey, N.J.) with a solution of CEKOL® 300 carboxymethylcellulose (CMC) available from Noviant B.V., Nijmegen, the Netherlands. Example 10 product has a median particle size of 5.8 μm, an oil absorption of 165 ml/100 g, a 5% pH of 9.79 and a BET surface area of 70 $M^2$/g.

For Example 11, the calcium silicate was coated in the Glatt fluid bed coater with a solution of Starch 1500 available from Colorcon, West Point, Pa. Example 11 product had a median particle size of 8.7 μm, an oil absorption of 166 ml/100 g, a 5% pH of 9.63 and a BET surface area of 80 $M^2/g$. Coating parameters for Example 10 and 11 are summarized below in Table 7.

For Control A, the same calcium silicate used for Example 10 and 11 was not coated.

TABLE 7

| Example | Coating | % Coating | Coating Rate ml/min | Air Velocity Setting | Inlet Temp. °C. |
|---|---|---|---|---|---|
| 10 | CEKOL ® 300 | 5 | 10-12 | 5 | 67 |
| 11 | Starch 1500 | 5 | 8-14 | 4 | 75 |
| Control A | None | Na | Na | Na | Na |

Example 10, Example 11, and the uncoated Control A were separately suspended in a 10% aqueous solution of aluminum chlorohydrate (ACH) available from Reheis, Inc., Berkeley Heights, N.J., stirred for 30 minutes, recovered by filtration, washed, and dried for 16 hr at 105° C. The samples were evaluated using GCMS to determine their ability to absorb isovaleric acid according to the low temperature GCMS method described previously. For comparison, a sample of uncoated calcium silicate that was not exposed to aluminum chlorohydrate (Control B) was also measured. Results of the evaluation are summarized in Table 8 below.

TABLE 8

| Example | Isovaleric acid μl/g | Portion Of Performance Retained Following ACH Exposure, % |
|---|---|---|
| Example 10 | 1006 | 57.2 |
| Example 11 | 1128 | 64.1 |
| Control A | 450 | 25.6 |
| Control B | 1760 | — |

Untreated calcium silicate Control A lost about 75% of its capacity to absorb isovaleric acid after exposure to a 10% aqueous solution of aluminum chlorohydrate. Application of 5% w/w of coatings of the present invention allowed over 60% of the capacity to be retained.

EXAMPLE 12

In this example, calcium silicate ($Ca_2SiO_4$ prepared as a precursor in Example 7-8) was coated with polyethylene glycol (Example 12) or left uncoated (Control). Specifically, 30 g calcium silicate was dispersed in deionized water and mixed at 10,000 rpm to a homogenous suspension using a Silverson homogenizer model L4RT-A, available from Silverson Machines, Inc., East Longmeadow, Mass. In a separate container, 10 g PEG (polyethylene glycol) and 5 g PPG 14 propylene glycol butyl ether (Americol B.V., the Netherlands) along with 1 g TWEEN® 20 (polyoxyethylenesorbitan monolaurate) available from ICI Americas, Inc., Wilmington, Del., was added to 300 g isopropyl alcohol (IPA). The IPA solution was added dropwise to the water suspension containing the calcium silicate particles while continuing to mix at 10,000 rpm. The final suspension was then added to a LAB-CONCO rotary vacuum evaporator and the vacuum vessel immersed in a water bath heated to 60° C. to remove the IPA. The temperature was increased to 80° C. and evaporation was continued until the dry coated particles could be removed as a free flowing powder.

The coated particles were tested for absorption capacity according to the methods described above and are summarized in Table 9 below.

TABLE 9

| Example | % Organic Treatment | Isovaleric Acid Capacity, μl/g | Isovaleric Acid Capacity, μl/g Calcium silicate |
|---|---|---|---|
| 12 | 30 | 1209 | 1727 |
| Control | 0 | 1767 | 1767 |

On an active pigment basis there was no loss in performance by applying the coating.

These samples were next dispersed at a level of 1% wt/wt in a 10% solution of an antiperspirant salt, aluminum/zirconium tetrachlorohydrex-Gly Summit AZG370 available from Summit Research Labs, Huguenot, N.Y. The dispersions were held at 25° C. until an interaction between the antiperspirant salt solution and silicate odor absorbent particles was observed. An interaction manifests itself as a visual thickening or gelling of the antiperspirant salt solution; the results evinced the inferiority of the control.

TABLE 10

| Example | % Organic Treatment | Days stability |
|---|---|---|
| 12 | 30 | >20 |
| Control | 0 | <7 |

EXAMPLES 13-15

In these examples, already formed calcium silicate was post-treated with different treatment amounts of CEKOL® 500T CMC and tested odor absorption properties. The calcium silicate was a 3.0 mole ratio $Ca_3SiO_5$ product produced by adding a total of 1052 liters of sulfuric acid at a concentration of 11.5% at a rate of 17.8 lpm (liters per minute) to 1893 liters of waterglass solution (3.3 $SiO_2/Na_2O$ mole ratio) containing 13% sodium silicate solids while mixing at a temperature of 95° C. The addition of the sulfuric acid was continued until a pH of 5.5 was obtained, and the reaction mixture was digested for 1 hr. The resulting suspension of silica particles was recovered by filtration, and dried overnight at 105° C. to form a finely divided reactive silica powder.

Next, 923.2 g reactive silica produced above was slurried in water to 14.56% solids in a reaction vessel equipped with a constant torque agitator and paddle blades. Then 200 g water and 3094.5 g lime slurry at 15.0% solids were added to the reactor along with 200 g rinse water used to rinse the lime slurry from its container. The reactor temperature was raised to 95° C. and the reaction mixture was digested for 60 minutes. The resulting calcium silicate was then filtered, dried and milled.

A portion of the 3.0 mole ratio $Ca_3:SiO_5$ prepared above was retained as a control. Another portion of the 3 mole ratio calcium silicate prepared above was treated with CMC by adding 100 g of the prepared calcium silicate to 900 g water in an agitated vessel using a constant torque agitator and paddle blades. To this slurry was added 33.4 g of 3% CEKOL® 500T CMC and 200 g water. The mixture was heated to 95° C. and digested for 60 minutes, before being recovered by filtration, then washed, and dried. This 3 mole ratio calcium silicate treated with 1% CMC was designated Example 13.

Another portion of $Ca_3SiO_5$ prepared above was treated with a different amount of CMC by adding 100 g calcium silicate to 900 g water in an agitated vessel using a constant torque agitator and paddle blades. To this slurry was added 167.0 g of 3% CEKOL® 500T CMC and 400 g water. The mixture was heated to 95° C. and digested for 60 minutes, before being recovered by filtration, then washed, and dried. This 3 mole ratio calcium silicate treated with 5% CMC was designated Example 14.

Another portion of the 3 mole ratio calcium silicate prepared above was treated with a different amount of CMC by adding 100 g calcium silicate to 900 g water in an agitated vessel using a constant torque agitator and paddle blades. To this slurry was added 334 g of 3% CEKOL® 500T CMC and 400 g water. The mixture was heated to 95° C. and digested for 60 minutes, before being recovered by filtration, then washed, and dried. This 3 mole ratio calcium silicate treated with 10% CMC was designated Example 15.

Examples 13-15 and an untreated 3 mole ratio calcium silicate control were tested for several properties according to the methods described above. The results are summarized in Table 11 below.

TABLE 11

| | Sample | | | |
|---|---|---|---|---|
| | Control | Example 13 | Example 14 | Example 15 |
| Treatment | None | 1% CMC | 5% CMC | 10% CMC |
| 5% pH | 11.76 | 11.8 | 11.77 | 11.8 |
| Odor Neutralization, μl/g | 2086 | 1795 | 1770 | 1700 |
| BET, M²/g | — | 42 | 54 | 58 |
| MPS, μm | — | 7.1 | 7.2 | 7.6 |

It is seen from the data above that all treatment levels provided improved odor neutralization as compared to the uncoated control calcium silicate.

EXAMPLE 16

In this example, magnesium silicate ($Mg_2SiO_4$) was prepared and treated with different organic films and then tested for odor neutralization. Reactive silica was made first by adding a total of 1052 liters of sulfuric acid at a concentration of 11.5% at a rate of 17.8 lpm (liters per minute) to 1893 liters of waterglass solution (3.3 $SiO_2/Na_2O$ mole ratio) containing 13% sodium silicate solids while mixing at a temperature of 95° C. The addition of the sulfuric acid was continued until a pH of 5.5 was obtained, and the reaction mixture was digested for 1 hr. The resulting suspension of silica particles was recovered by filtration, and dried overnight at 105° C. to form a finely divided reactive silica powder.

The reactive silica produced above was slurried in water to 14.56% solids. Then 200 g water and 461.5 g of the silica slurry (14.56% solids) were mixed in a reaction vessel equipped with a constant torque agitator and paddle blades. To this mixture was added 220.78 g magnesium hydroxide slurry at 51% solids along with 300 g rinse water used to rinse the $Mg(OH)_2$ slurry from the beaker. The reactor temperature was raised to 90° C. and the reaction mixture digested for 60 minutes. The resulting (2:1 mole ratio) magnesium silicate was then filtered and the filter cake (wet cake) was retained for further coating. A portion of the wet cake was dried overnight at 150° C., milled to 7.7 μm and designated as Example 16 control. Example 16 Control has an oil absorption of 76 ml/100 g and a BET surface area of 43 $M^2/g$, The formed magnesium silicate was next coated with various organic films and evaluated for odor neutralization. The coating was prepared by combining 128 g of the magnesium silicate wet cake (38.9% solids) prepared above, 420 g water and 250 g of a 1% CEKOL® 2000 CMC solution. The mixture was heated to 95° C. and digested for 1 hour. The CMC coated magnesium silicate was recovered by filtration and dried overnight at 105° C. and is designated as Example 16A.

The formed magnesium silicate was next coated with isostearic acid by combining 46.27 g of the magnesium silicate wet cake (38.9% solids) prepared above and 2.0 g isostearic acid and mixing until the mixture began a homogenous fluid. The mixture was then dried overnight at 105° C. and the dried isostearic acid coated magnesium silicate is designated as Example 16B. Several properties of Example 16 Control, Example 16A and Example 16B were measured according to the methods described above and are summarized below in Table 12.

TABLE 12

| | Sample | | |
|---|---|---|---|
| | Example 16 Control | Example 16A | Example 16B |
| Treatment | None | 5% CMC | 10% Isostearic Acid |
| 5% pH | 8.80 | 9.47 | 9.13 |
| Odor Neutralization, μl/g | 1925 | 1428 | 1075 |

EXAMPLE 17

In this example, calcium magnesium silicate ($Ca_{0.5}Mg_{1.5}SiO_4$) was prepared by first forming reactive silica as described in Example 16. The reactive silica was slurried in water to 14.56% solids and 461.6 g of this slurry and 200 g water were mixed together and then 165.6 g magnesium hydroxide slurry (51% solids) was added. The mixture was digested for 5 minutes and then 258.4 g lime slurry (16.19% solids) and 200 g water used to rinse the beaker containing the lime slurry was added. The mixture was heated to 90° C. and digested for 1 hour. The resulting calcium magnesium silicate was then filtered and the filter cake (wet cake) was retained for further coating. A portion of the wet cake was dried overnight at 150° C., milled and designated as Example 17 Control. Example 17 Control has an oil absorption of 120 ml/100 g and a BET surface area of 124 $M^2/g$.

The formed calcium magnesium silicate was next coated with various organic films and evaluated for odor neutralization. The coating was prepared by combining 253.8 g of the calcium magnesium silicate wet cake (19.7% solids) prepared above, 296.1 g water and 250 g of a 1% CEKOL® 2000 CMC solution. The mixture was heated to 95° C. and digested for 1 hour. The CMC coated calcium magnesium silicate was recovered by filtration and dried overnight at 105° C. and is designated as Example 17A.

The formed calcium magnesium silicate was next coated with isostearic acid by combining 91.4 g of the calcium magnesium silicate wet cake (19.7% solids) prepared above and 2.0 g isostearic acid and mixing until the mixture began a homogenous fluid. The mixture was then dried overnight at 105° C. and the dried isostearic acid coated calcium magnesium silicate is designated as Example 17B. Several properties of Example 17 Control, Example 17A and Example 17B were measured according to the methods described above and are summarized below in Table 13.

TABLE 13

| | Sample | | |
|---|---|---|---|
| | Example 17 Control | Example 17A | Example 17B |
| Treatment | None | 5% CMC | 10% Isostearic Acid |
| 5% pH | 9.48 | 9.51 | 9.72 |
| Odor Neutralization, µl/g | 1851 | 877 | 738 |

EXAMPLE 18

In this example a magnesium zinc silicate ($MgZnSiO_4$) was prepared, treated with different organic films and then tested for odor neutralization. The zinc sulfate reactant was prepared by mixing 287.54 g $ZnSO_4.7H_2O$ and 700 g water and then heating the mixture to 60° C. with mixing to dissolve the zinc sulfate. The sodium silicate reactant was prepared by diluting 1280 g of a 3.3 mole ratio sodium silicate solution (waterglass) at 21% solids with 741 g water to a final concentration of 13.3%. Zinc silicate was formed by adding the zinc sulfate reactant to the sodium silicate solution formed above at a rate of 29 ml/min for 30 minutes. The mixture was then digested for 15 minutes. The resulting zinc silicate was recovered by filtration, reslurried in hot water, refiltered, and washed with hot water. To form the magnesium zinc silicate, 1365 g of the zinc silicate filter cake (20.3% solids) previously prepared was slurried with 300 g water and then 272 g $Mg(OH)_2$ solution at 51% solids was added. The mixture was heated to 90° C. and digested for 1 hour. The resulting magnesium zinc silicate was then filtered and the filter cake (wet cake) was retained for further coating. A portion of the filter cake was dried overnight at 150° C., milled and designated as Example 18 Control. Example 18 Control had an oil absorption of 72 ml/100 g and a BET surface area of 23 $M^2/g$.

The formed magnesium zinc silicate was next coated with various organic films and evaluated for odor neutralization. The coating was prepared by combining 158.7 g of the magnesium zinc silicate filter cake (31.5% solids) prepared above, 391.3 g water and 250 g of a 1% CEKOL® 2000 CMC solution. The mixture was heated to 95° C. and digested for 1 hour. The CMC coated magnesium zinc silicate was recovered by filtration and dried overnight at 105° C. and is designated as Example 18A.

The formed magnesium zinc silicate was next coated with isostearic acid by combining 57.1 g of the calcium magnesium silicate wet cake (31.5% solids) prepared above and 2.0 g isostearic acid and mixing until the mixture began a homogenous fluid. The mixture was then dried overnight at 105° C. and the dried isostearic acid coated magnesium zinc silicate is designated as Example 18B. Several properties of Example 18 Control, Example 18A and Example 18B were measured according to the methods described above and are summarized below in Table 14.

TABLE 14

| | Sample | | |
|---|---|---|---|
| | Example 18 Control | Example 18A | Example 18B |
| Treatment | None | 5% CMC | 10% Isostearic Acid |
| 5% pH | 9.33 | 9.51 | — |
| Odor Neutralization, µl/g | 1419 | 1107 | 911 |

We claim:

1. A personal care composition comprising i) at least one antiperspirant salt, and ii) at least one particulate amorphous metal silicate material that is at least partially coated with an organic film, wherein said organic film is comprised of at least one hydrophobic material, wherein said hydrophobic material is selected from the group consisting of polyvinyl acetate, water-insoluble polyacrylamide, polyvinyl chloride, polystyrene, polyethylene, polymethacrylate, paraffin wax, carnauba wax, beeswax, stearyl alcohol, zein, shellac, edible fat, fatty acids, alkali metal salts of fatty acids, and any combinations thereof; and wherein said organic film exhibits either a) an ability to erode when subjected to sufficient pH changes or b) sufficient porosity to permit migration of metal ions or isovaleric acid therethrough; and iii) optionally, at least one dermatologically acceptable vehicle.

2. The personal care composition of claim 1 and wherein said at least one dermatologically acceptable vehicle is present and is selected from the group consisting of an aqueous vehicle, a non-aqueous vehicle, or a combination of both.

3. The personal care composition of claim 2 wherein said vehicle is selected from the group consisting of water, at least one water-miscible organic liquid, at least one dispersible organic liquid, at least one water-immiscible liquid, at least one wax, and any combinations thereof.

4. The personal care composition of claim 1 wherein said metal silicate material is represented by the formula $Ca_xM_ySiO_z$, wherein M is one or more multivalent cations selected from Mg, Al, and Zn, and x is the number of moles of the calcium cations and is between 0 and 4, y is the number of moles of such other metal cations and is between 0 and 4, z is the number of moles required to balance the overall charge of the metal cations, and x+y is from 1 to 6.

5. The personal care composition of claim 4 wherein said metal silicate material is selected from the group consisting of calcium silicate, calcium magnesium silicate, calcium zinc silicate, magnesium silicate, magnesium zinc silicate, and calcium aluminosilicate.

6. The personal care composition of claim 5 wherein said metal silicate material is calcium silicate.

7. The personal care composition of claim 1 wherein said antiperspirant is salt selected from the group consisting of aluminum halides, aluminum hydroxy-halides, zirconium oxy salts, zirconium hydroxy salts, and any mixtures thereof.

8. The personal care composition of claim 7 wherein said antiperspirant salt is selected from the group consisting of aluminum chloride; aluminum hydroxyhalides corresponding with the formula $Al_2(OH)_xQ_y.XH_2O$ where Q is chlorine, bromine or iodine, wherein x is from about 2 to about 5, and x+y=about 6, and x and y do not need to be integers, and where X is from about 1 to about 6; zirconium oxy salts; zirconium hydroxy salts represented by the general empirical formula:

wherein z may vary from about 0.9 to about 2 and need not be an integer, n is the valence of B, 2-nz is greater than or equal to 0, and B may be selected from the group consisting of halides, nitrate, sulfamate, sulfate; and any mixtures thereof.

9. The personal care composition of claim 4 wherein component ii) is an antiperspirant salt selected from the group consisting of aluminum halides, aluminum hydroxy-halides, zirconium oxy salts, zirconium hydroxy salts, and any mixtures thereof.

10. The personal care composition of claim 9 wherein said antiperspirant salt is selected from the group consisting of aluminum chloride; aluminum hydroxyhalides corresponding with the formula $Al_2(OH)_xQ_y \cdot XH_2O$ where Q is chlorine, bromine or iodine, wherein x is from about 2 to about 5, and x+y=about 6, and x and y do not need to be integers, and where X is from about 1 to about 6; zirconium oxy salts; zirconium hydroxy salts represented by the general empirical formula:

$$ZrO(OH)_{2-nz}B_z$$

wherein z may vary from about 0.9 to about 2 and need not be an integer, n is the valence of B, 2-nz is greater than or equal to 0, and B may be selected from the group consisting of halides, nitrate, sulfamate, sulfate; and any mixtures thereof.

11. A method of inhibiting body odor by applying to a person's skin an effective amount of the personal care composition of claim 7.

12. A method of inhibiting body odor by applying to a person's skin an effective amount of the personal care composition of claim 9.

* * * * *